United States Patent [19]
Thornton

[11] Patent Number: 6,102,931
[45] Date of Patent: Aug. 15, 2000

[54] INTRAVASCULAR DEVICE FOR VENTING AN INFLATABLE CHAMBER

[75] Inventor: Peter Thornton, Los Altos, Calif.

[73] Assignee: Embol-X, Inc., Mountain View, Calif.

[21] Appl. No.: 09/370,674

[22] Filed: Aug. 9, 1999

[51] Int. Cl.$^7$ ................................................. A61M 29/00
[52] U.S. Cl. .......................................... 606/194; 604/96
[58] Field of Search ................................. 606/194, 192; 604/96, 102, 101

[56] References Cited

U.S. PATENT DOCUMENTS

| | | | |
|---|---|---|---|
| 5,151,087 | 9/1992 | Jonkman | 604/164 |
| 5,830,181 | 11/1998 | Thornton | 604/96 |
| 5,989,218 | 11/1999 | Wasicek | 604/96 |
| 6,007,517 | 12/1999 | Anderson | 606/194 |

*Primary Examiner*—Michael Buiz
*Assistant Examiner*—Kevin Truong
*Attorney, Agent, or Firm*—Lyon & Lyon LLP

[57] ABSTRACT

An intravascular device for venting an inflatable chamber and methods for using the device are disclosed. The intravascular device generally includes three components, namely a catheter or cannula, an inflatable member, and a selective degassing element. The inflatable member is typically a balloon. The catheter or cannula is typically hollow with a first lumen extending between an inflation port and the interior of the inflatable member and a second lumen extending between the interior of the inflatable member and an exhaust port. The selective degassing element is typically positioned between the inflatable member and the exhaust port and occupies the entire cross-sectional area of the second lumen. When in a closed position, the selective element prevents the passage of liquid from the interior of the inflatable member, through the exhaust port. When in an open position, the selective element permits gas entrained within the inflatable member to be expelled from the device, via the exhaust port.

27 Claims, 6 Drawing Sheets

6,102,931

INTRAVASCULAR DEVICE FOR VENTING AN INFLATABLE CHAMBER

FIELD OF THE INVENTION

The present invention relates generally to intravascular devices that incorporate an inflatable member, and more particularly to devices of this type which enable rapid and efficient degassing of the device. The present invention also relates to methods for rapidly and efficiently degassing an intravascular device that incorporates an inflatable member.

BACKGROUND OF THE INVENTION

During the course of many medical procedures, it is often necessary to introduce a catheter or cannula that incorporates an inflatable member, such as a balloon catheter, into the circulatory system of the patient. However, before such a device can be safely utilized, the physician, or other qualified medical personnel, must institute a degassing process. That is, gasses, such as air, entrained in the device during manufacturing and packaging must be displaced so that if the inflatable member should leak or rupture during use, the chance of gas being released into the circulatory system is minimized.

For example, when utilizing PTCA catheters or intra-aortic balloon occlusion catheters/cannula, medical personnel must typically perform repeated liquid inflation and deflation cycles prior to placement of the device, in an effort to remove all entrapped air from the inflatable member. This tedious process is often difficult to accomplish. Furthermore, the degassing process is time consuming, inconvenient, and costly.

The need to perform numerous inflation and deflation cycles in an effort to remove all entrained gasses can also severely limit the design of the overall device. In particular, intravascular devices that have a large volume of inflation tubing in comparison to the overall volume of the inflatable member tend to be especially difficult to degas.

Accordingly, there is a need for an intravascular device that incorporates an inflatable member, such as a balloon catheter, which permits rapid and efficient degassing of the device. Furthermore, there is a need for such a device which also places few, if any, restrictions on design choices. The present invention satisfies both of these needs.

SUMMARY OF THE INVENTION

The present invention relates to medical devices and their methods of use, particularly intravascular catheters and cannula which incorporate an inflatable member. The intravascular device of the present invention generally includes three components, namely: (1) a catheter or cannula; (2) an inflatable member; and (3) a selective degassing element.

The inflatable member is typically a balloon having a defined interior. The balloon is capable of expansion to a defined volume when the interior of the balloon is infused with liquid.

The catheter or cannula is typically hollow. The proximal end of the catheter or cannula incorporates an inflation port. The distal end of the catheter or cannula incorporates an exhaust port. A first lumen extends within the catheter or cannula from the inflation port to the interior of the inflatable member. A second lumen extends within the catheter or cannula from the exhaust port to the interior of the inflatable member. The first lumen enables liquid, infused into the catheter or cannula through the inflation port, to flow into the interior of the inflatable member. The second lumen enables gas, entrained within the interior of the inflatable member, to be expelled from the catheter or cannula through the exhaust port.

The selective degassing element typically occupies the entire cross-sectional area of the second lumen and is preferably positioned across the second lumen near the exhaust port. When in a closed position, the selective element prevents the passage of liquid from the interior of the inflatable member, through the exhaust port, via the second lumen. However, when the selective element is in an open position, the gas entrained within the inflatable member is permitted to pass through the second lumen to the exhaust port. This flow of gas may be expedited, in some instances, by the infusion of liquid into the device through the inflation port—causing any gas entrained within the first lumen, the second lumen, or the interior of the inflatable member to migrate toward the selective degassing element, pass through the selective degassing element, and be expelled from the catheter or cannula through the exhaust port.

The selective degassing element can take a number of forms and can be placed in an open or closed position in a number of ways. In certain embodiments, the selective degassing element is a non-mechanically actuated valve, a plug, a membrane, a mechanically actuated valve, or a hydrophobic filter. The non-mechanically actuated valve, the plug, and the membrane are typically in a closed position unless placed in an open position by insertion of a needle or hollow tube. The hydrophobic filter is always in an open position.

DETAILED DESCRIPTION OF THE PREFERRED EMBODIMENTS

Figure 1:
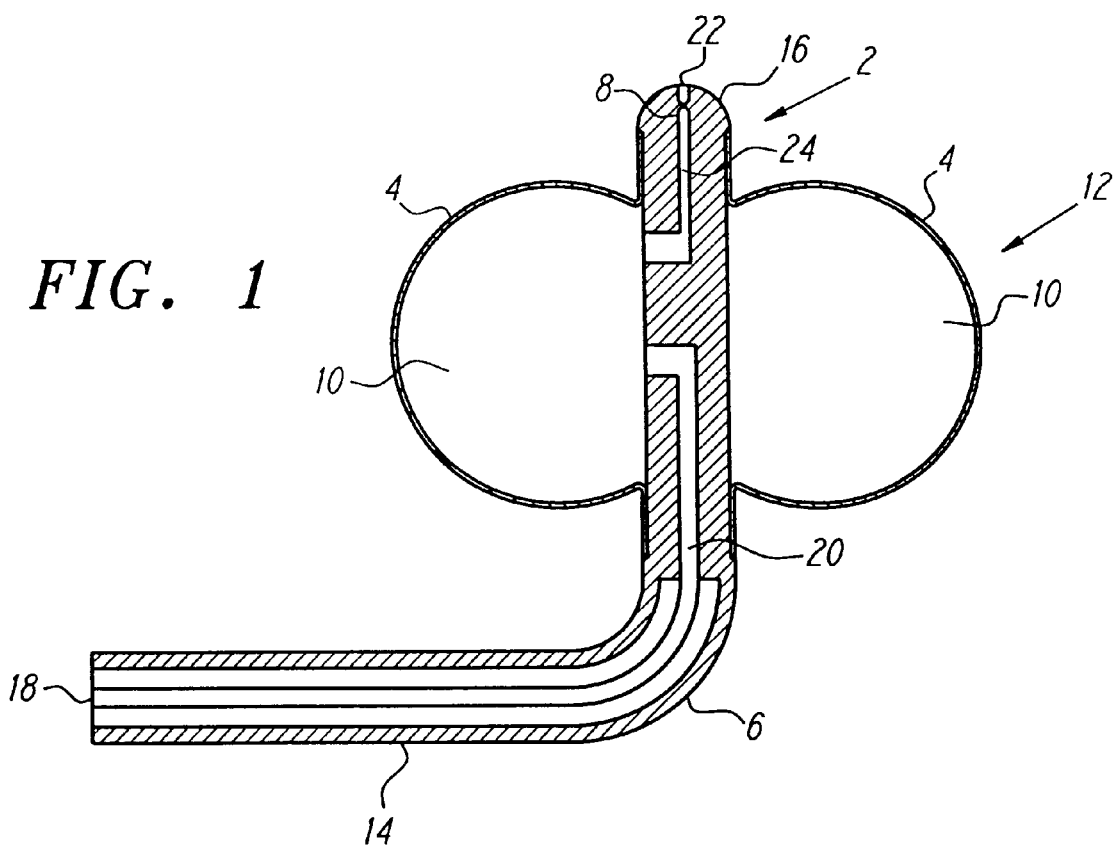
FIG. 1 is a cross-sectional view of one preferred embodiment of the present invention.

Turning now to the drawings, FIGS. 1–10 show various preferred embodiments of the present invention. As shown in FIG. 1, the intravascular device 2 of the present invention generally includes three components, namely an inflatable member 4, a catheter or cannula 6, and a selective degassing element 8.

The inflatable member 4 is typically a balloon having a defined interior 10 and exterior 12. The inflatable member 4 is capable of expansion to a defined volume when the interior 10 of the inflatable member 4 is infused with liquid.

The catheter or cannula 6 is typically hollow and has a proximal 14 and a distal 16 end. The proximal end 14 incorporates an inflation port 18. A first lumen 20 extends within the catheter or cannulae 6 from the inflation port 18 to the interior 10 of the inflatable member 4. This first lumen 20 enables liquid, infused into the catheter or cannula 6 through the inflation port 18, to flow into the interior 10 of the inflatable member 4. The distal end 16 incorporates an exhaust port 22. A second lumen 24 extends within the catheter or cannula 6 from the exhaust port 22 to the interior 10 of the inflatable member 4. This second lumen 24 enables gas, entrained within the interior 10 of the inflatable member 4, to be expelled from the catheter or cannula 6 through the exhaust port 22.

The selective degassing element 8 typically occupies the entire cross sectional area of the second lumen 24. Preferably, the selective element 8 is positioned across the second lumen 24 near the exhaust port 22. When liquid is infused through the inflation port 18, any gas entrained within the first lumen 20, the interior 10 of the inflatable member 4, or the second lumen 24 (between the interior 10 of the inflatable member 4 and the selective degassing element 8), is allowed to pass through the exhaust port 22 when the selective element 8 is in the open position.

Figure 2:
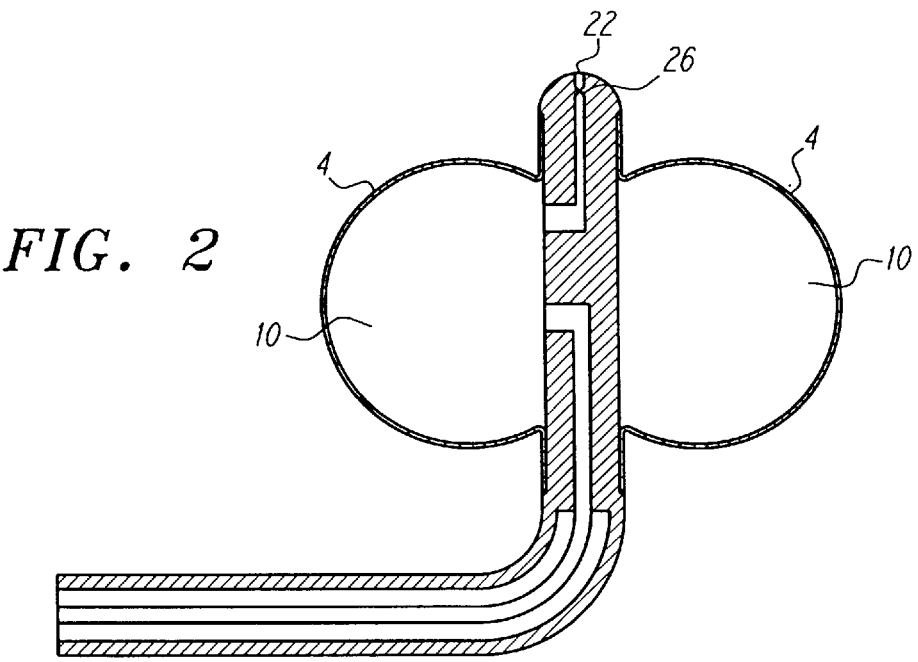
FIG. 2 is another cross-sectional view of one preferred embodiment of the present invention illustrating the non-mechanically actuated valve in a closed configuration.

As shown in FIG. 2, the selective element of the first preferred embodiment of the present invention is a non-mechanically actuated valve 26. Such a non-mechanically actuated valve 26 can be manufactured from a variety of materials which should be obvious to those of ordinary skill in the art. Preferably, the non-mechanically actuated valve 26 of the first preferred embodiment of the present invention is manufactured from slited rubber or a self-sealing elastomer. The non-mechanically actuated valve 26 is typically maintained in a closed position—preventing the passage of liquid from the interior 10 of the inflatable member 4, through the exhaust port 22.

Figure 3:
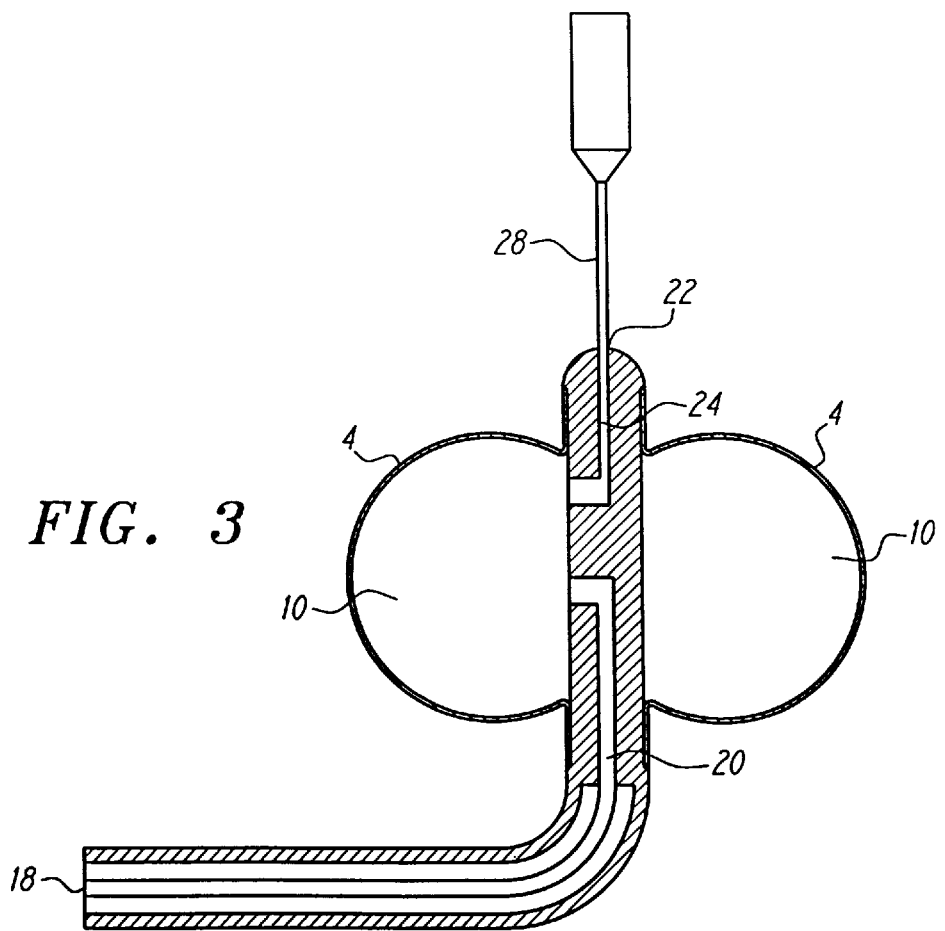
FIG. 3 is a cross-sectional view of one preferred embodiment of the present invention illustrating the non-mechanically actuated valve in an open configuration.

However, as shown in FIG. 3, when a needle or hollow tube 28 is inserted into the non-mechanically actuated valve 26, the non-mechanically actuated valve 26 is placed in an open position and a passage is formed for the escape of gas from the first lumen 20, the second lumen 24, and the interior 10 of the inflatable member 4 through the exhaust port 22. This escape of gas may be aided by flushing the first lumen 20, the second lumen 24, and the interior 10 of the inflatable member 4 with large volumes of liquid through the inflation port 18, with the liquid flow helping direct the entrapped gasses through the non-mechanically actuated valve 26 and the exhaust port 22. When the needle or hollow tube 28 is withdrawn from the non-mechanically actuated valve 26, the non-mechanically actuated valve 26 is returned to a closed position.

Figure 4:
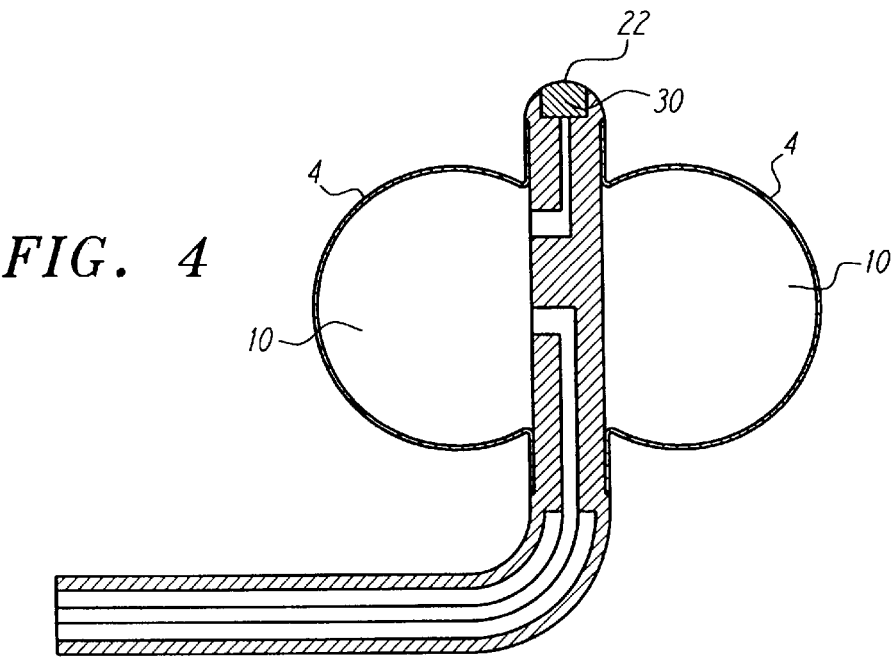
FIG. 4 is a cross-sectional view of a second preferred embodiment of the present invention illustrating the plug in a closed configuration.

As shown in FIG. 4, the selective degassing element of the second preferred embodiment of the present invention is a plug 30. Such a plug 30 can be manufactured from a variety of materials which should be obvious to those of ordinary skill in the art. Preferably, the plug 30 of the second preferred embodiment of the present invention is manufactured from latex, silicone rubber or other "self-heating" material. The plug 30 is typically maintained in a closed position—preventing the passage of liquid from the interior 10 of the inflatable member 4, through the exhaust port 22.

Figure 5:
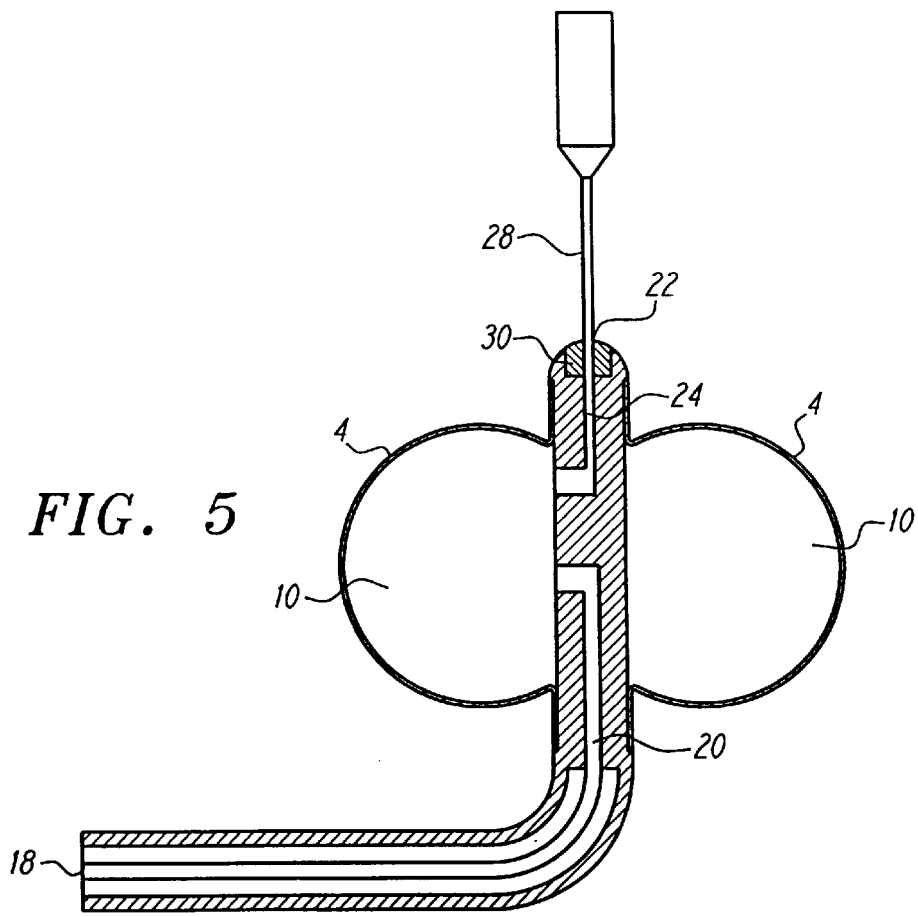
FIG. 5 is a cross-sectional view of a second preferred embodiment of the present invention illustrating the plug in an open configuration.

However, as shown in FIG. 5, when a needle or hollow tube 28 is inserted through the plug 30, the plug 30 is placed in an open position and a passage is formed for the escape of gas from the first lumen 20, the second lumen 24, and the interior 10 of the inflatable member 4 through the exhaust port 22. This escape of gas may be aided by flushing the first lumen 20, the second lumen 24, and the interior 10 of the inflatable member 4 with large volumes of liquid through the inflation port 18, with the liquid flow helping direct the entrapped gasses through the plug 30 and the exhaust port 22. When the needle or hollow tube 28 is withdrawn from the plug 30, the plug 30 is returned to a closed position.

Figure 6:
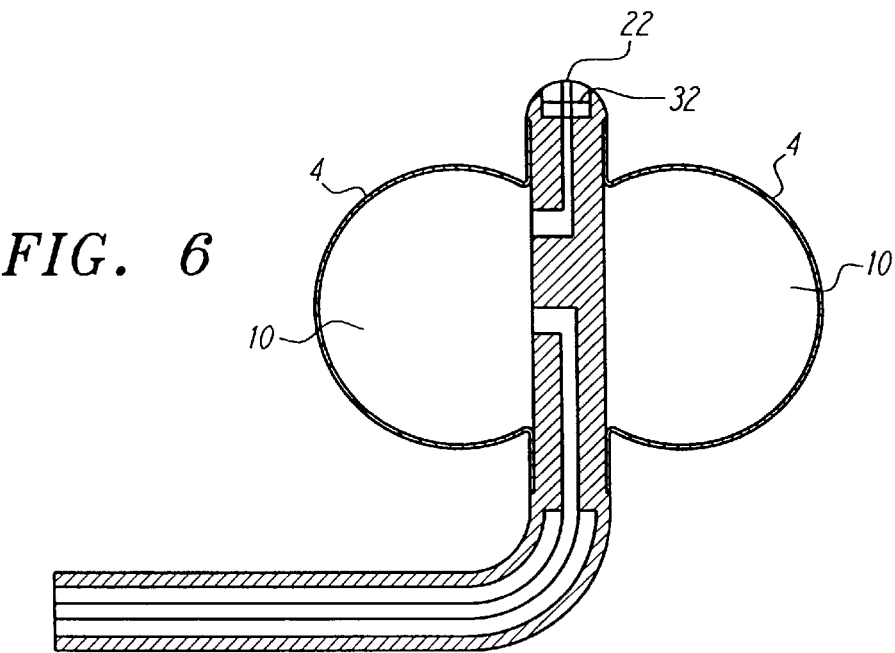
FIG. 6 is a cross-sectional view of a third preferred embodiment of the present invention illustrating the membrane in a closed configuration.

As shown in FIG. 6, the selective degassing element of the third preferred embodiment of the present invention is a membrane 32. Such a membrane 32 can be manufactured from a variety of materials which should be obvious to those of ordinary skill in the art. Preferably, the membrane 32 of the third preferred embodiment of the present invention is manufactured from Gortex or nylon mesh. The membrane 32 is typically maintained in a closed position—preventing the passage of liquid from the interior 10 of the inflatable member 4, through the exhaust port 22.

Figure 7:
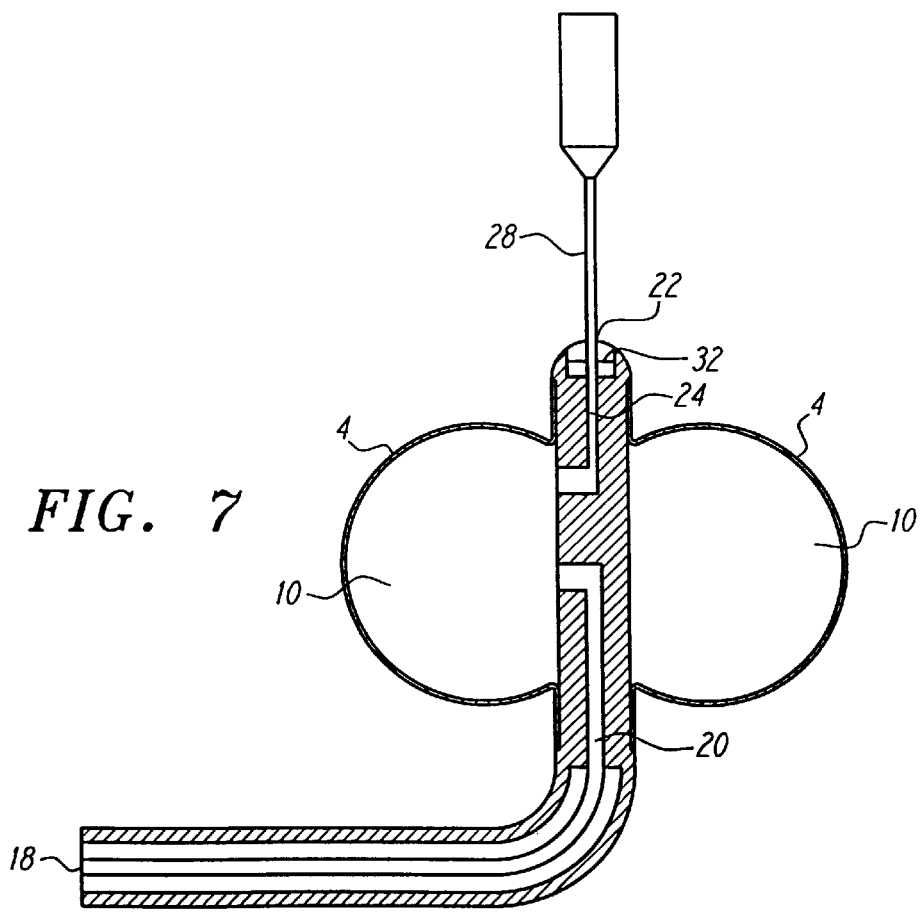
FIG. 7 is a cross-sectional view of a third preferred embodiment of the present invention illustrating the membrane in an open configuration.

However, as shown in FIG. 7, when a needle or hollow tube 28 is inserted through the membrane 32, the membrane 32 is placed in an open position and a passage is formed for the escape of gas from the first lumen 20, the second lumen 24, and the interior 10 of the inflatable member 4 through the exhaust port 22. This escape of gas may be aided by flushing the first lumen 20, the second lumen 24, and the interior 10 of the inflatable member 4 with large volumes of liquid through the inflation port 18, with the liquid flow helping direct the entrapped gasses through the membrane 32 and the exhaust port 22. When the needle or hollow tube 28 is withdrawn from the membrane 32, the membrane 32 is returned to a closed position.

Figure 8:
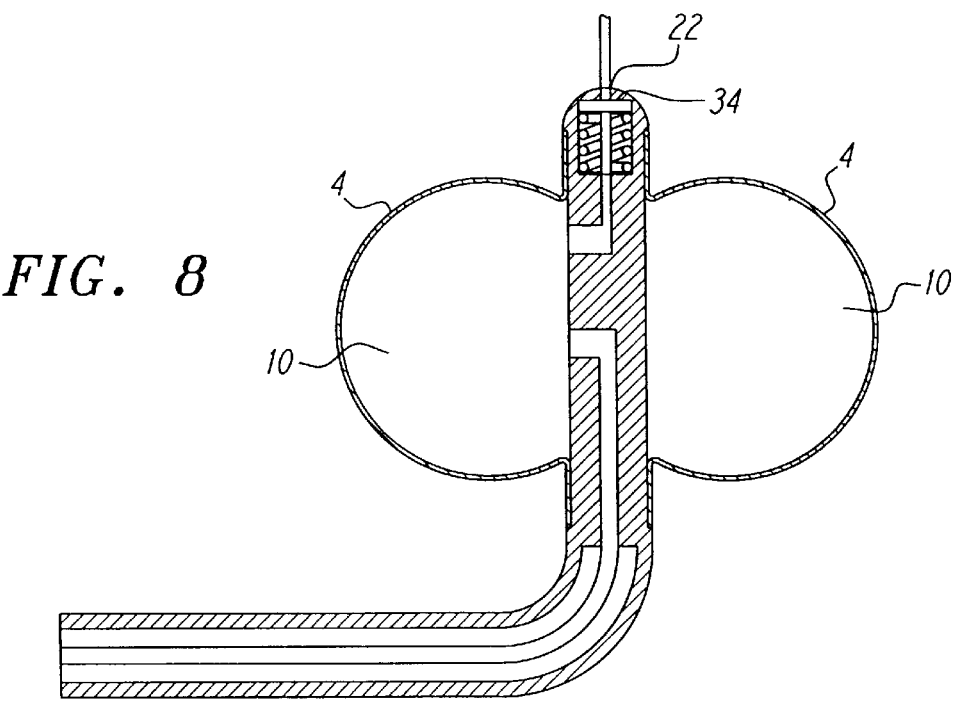
FIG. 8 is a cross-sectional view of a fourth preferred embodiment of the present invention illustrating the mechanically actuated valve in a closed configuration.

As shown in FIG. 8, the selective degassing element of the fourth preferred embodiment of the present invention is a mechanically actuated valve 34. Such a mechanically actuated valve 34 can be selected from a variety of valves which should be obvious to those of ordinary skill in the art. Preferably, the mechanically actuated valve 34 of the fourth preferred embodiment of the present invention is a one-way check valve. The mechanically actuated valve 34 is typically maintained in a closed position—preventing the passage of liquid from the interior 10 of the inflatable member 4, through the exhaust port 22.

Figure 9:
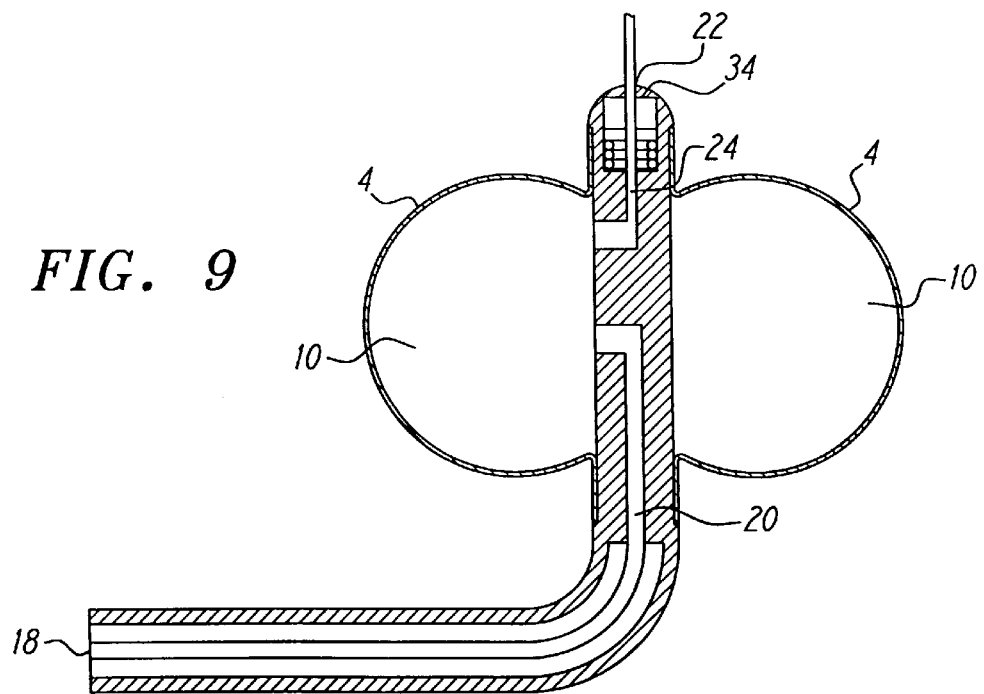
FIG. 9 is a cross-sectional view of a fourth preferred embodiment of the present invention illustrating the mechanically actuated valve in an open configuration.

However, as shown in FIG. 9, when the mechanically actuated valve 34 is placed in an open position, a passage is formed for the escape of gas from the first lumen 20, the second lumen 24, and the interior 10 of the inflatable member 4 through the exhaust port 22. This escape of gas may be aided by flushing the first lumen 20, the second lumen 24, and the interior 10 of the inflatable member 4 with large volumes of liquid through the inflation port 18, with the liquid flow helping direct the entrapped gasses through the mechanically actuated valve 34 and the exhaust port 22. When the mechanically actuated valve 34 is returned to a closed position, the flow of liquid or gas through the exhaust port 22 will cease.

Figure 10:
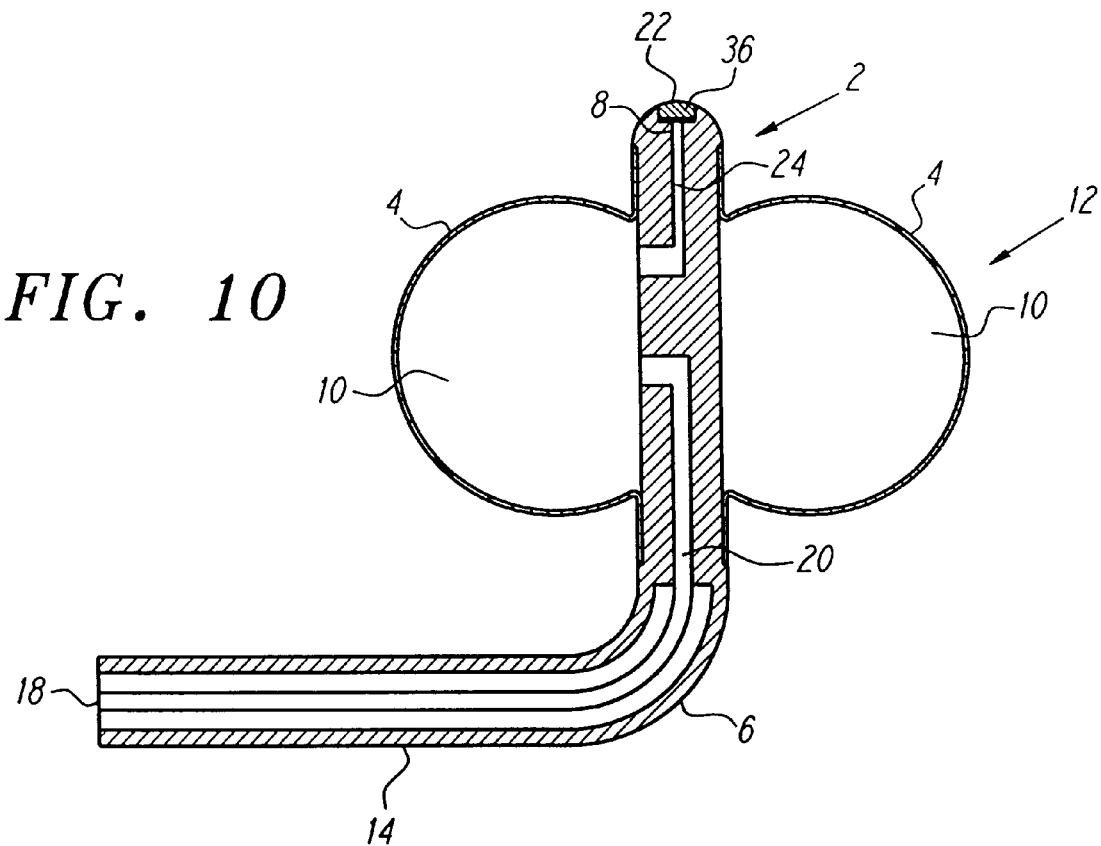
FIG. 10 is a cross-sectional view of a fifth preferred embodiment of the present invention.

As shown in FIG. 10, the selective degassing element of the fifth preferred embodiment of the present invention is a hydrophobic filter 36. Such a hydrophobic filter 36 is preferably a gas permeable, liquid impermeable, membrane or plug material. When liquid is infused through the inflation port 18, any gas entrained in the first lumen 20, the second lumen 24, or the interior 10 of the inflatable member 4 migrates toward the hydrophobic filter 36. The gas then selectively passes through the hydrophobic filter 36 and the exhaust port 22. The hydrophobic filter 36 is always in an open position.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An intravascular device, comprising:
   an elongate member having a proximal end, a distal end, and a distal region;
   a balloon having an interior chamber and being mounted on the distal region of the elongate member;
   an inflation tube having an inflation lumen communicating with the interior of said balloon and an inflation port, said inflation lumen for infusing a liquid into the balloon;
   a venting tube having a venting lumen communicating with the interior of said balloon and an exhaust port, said venting lumen for expulsion of gas from the interior of said balloon through said exhaust port;
   a selective degassing element, positioned across said venting lumen for the expulsion of gas from the balloon through said exhaust port and for preventing the expulsion of liquid from the balloon through said exhaust port.

2. The intravascular device of claim 1, wherein said elongate member is a catheter.

3. The intravascular device of claim 2, wherein said selective degassing element is a non-mechanically actuated valve.

4. The intravascular device of claim 4, wherein said valve is manufactured from slited rubber.

5. The intravascular device of claim 3, wherein said valve is manufactured from a self sealing elastomer.

6. The intravascular device of claim 2, wherein said selective degassing element is a plug.

7. The intravascular device of claim 6, wherein said plug is manufactured from sintered polyetheyene.

8. The intravascular device of claim 2, wherein said selective degassing element is a membrane.

9. The intravascular device of claim 8, wherein said membrane is manufactured from Gortex.

10. The intravascular device of claim 8, wherein said membrane is manufactured from nylon mesh.

11. The intravascular device of claim 2, wherein said selective degassing element is a mechanically actuated valve.

12. The intravascular device of claim 11, wherein said valve is a one-way check valve.

13. The intravascular device of claim 2, wherein said selective degassing element is a hydrophobic filter.

14. The intravascular device of claim 13, wherein said filter is a gas permeable membrane.

15. The intravascular device of claim 2, wherein said selective degassing element allows the expulsion of gas and liquid from the interior of said balloon through said exhaust port when said selective degassing element is in an open position, and prevents the expulsion of gas and liquid from the interior of said balloon through said exhaust port when said selective degassing element is in a closed position.

16. The intravascular device of claim 2, wherein said selective degassing element is capable of simultaneously allowing the expulsion of gas from the interior of said balloon through said exhaust port while preventing the expulsion of liquid from the interior of said balloon through said exhaust port.

17. The intravascular device of claim 1, wherein said elongate member is a cannula.

18. An intravascular device, comprising:
    an inflatable member having an interior and an exterior;
    a first lumen connecting the interior of said inflatable member and the exterior of said inflatable member, said first lumen capable of allowing the infusion of liquid from the exterior of said inflatable member into the interior of said inflatable member;
    a second lumen connecting the interior of said inflatable member and the exterior of said inflatable member, said second lumen capable of allowing the expulsion of gas from the interior of said inflatable member to the exterior of said inflatable member;
    a selective degassing element, said element positioned across said second lumen and capable of allowing the expulsion of gas from the interior of said inflatable member to the exterior of said inflatable member through said second lumen and capable of preventing the expulsion of liquid from the interior of said inflatable member to the exterior of said inflatable member through said second lumen.

19. An intravascular device, comprising:
    a catheter or cannula;
    a balloon attached to said catheter or cannula, said balloon having an interior and an exterior;
    a first lumen within said catheter or cannula, said first lumen connecting the interior of said balloon and an inflation port and capable of allowing the infusion of liquid through said inflation port into the interior of said balloon;
    a second lumen within said catheter or cannula, said second lumen connecting the interior of said balloon and an exhaust port and capable of allowing the expulsion of gas from the interior of said balloon through said exhaust port;
    a selective degassing element, said element positioned across said second lumen and capable of allowing the expulsion of gas from the interior of said balloon through said exhaust port and capable of preventing the expulsion of liquid from the interior of said balloon through said exhaust port.

20. A method for degassing an intravascular device, comprising the steps of:
    providing an elongate member having a proximal region and a distal region, a balloon mounted on the distal region, an inflation tube communicating with the interior of said balloon and an inflation port, a venting tube communicating with the interior of said balloon and an exhaust port, and a selective degassing element, said element positioned within said venting lumen for expulsion of gas from said balloon through said exhaust port and for preventing the expulsion of liquid from said balloon through said exhaust port;
    opening said degassing element; and
    injecting liquid into said balloon, wherein gas is purged from the balloon through said venting lumen, through said degassing element, and through said exhaust port.

21. The method of claim 20, wherein said selective degassing element is placed in an open position by inserting a needle or hollow tube into said element.

22. The method of claim 20, wherein said selective degassing element is placed in an open position by inserting a needle or hollow tube through said element.

23. The method of claim 20, wherein the elongate member in a cannula.

24. The method of claim 20, wherein the elongate member is a catheter.

25. The method of claim 20, wherein the selective degassing element is a non-mechanical valve.

26. The method of claim 20, wherein the selective degassing element is a mechanical valve.

27. The method of claim 25, wherein the valve is selected from the group consisting of slited rubber, self sealing elastomer, a plug, a membrane, and a hydrophobic filter.

* * * * *